United States Patent [19]

Moore

[11] Patent Number: 4,616,629

[45] Date of Patent: Oct. 14, 1986

[54] COIL CONSTRUCTION FOR ELECTROMAGNETIC TREATMENT OF AN AFFLICTED BODY REGION

[75] Inventor: John S. Moore, Upper Montclair, N.J.

[73] Assignee: Electro-Biology, Inc., Fairfield, N.J.

[21] Appl. No.: 737,433

[22] Filed: May 24, 1985

[51] Int. Cl.[4] .............................................. A61N 1/42
[52] U.S. Cl. .................................... 128/1.5; 128/82.1; 128/419 F
[58] Field of Search ................... 128/1.5, 82.1, 419 F, 128/804, 422

[56] References Cited

U.S. PATENT DOCUMENTS

| | | | |
|---|---|---|---|
| 3,890,953 | 6/1975 | Kraus et al. | 128/419 F |
| 3,915,151 | 10/1975 | Kraus | 128/419 F |
| 4,056,097 | 11/1977 | Maass | 128/419 F |
| 4,412,540 | 11/1983 | Bentall | 128/422 |

FOREIGN PATENT DOCUMENTS

| | | | |
|---|---|---|---|
| 51997 | 8/1936 | Denmark | 128/1.5 |
| 1103883 | 6/1955 | France | 128/422 |

OTHER PUBLICATIONS

General Electric X-Ray Corporation, Publication No. 7P–158, 4 pp. (date unknown).

Primary Examiner—William E. Kamm
Attorney, Agent, or Firm—Hopgood, Calimafde, Kalil, Blaustein & Judlowe

[57] ABSTRACT

The invention contemplates a single-coil configuration adapted for embedment in an orthopedic cast, for use in applying electromagnetic signals for osteogenic therapy. An otherwise flat circular multiple-turn coil is so permanently deformed as to establish a first generally U-shaped projection of the coil in a first viewing aspect which is normal to the coil axis, the deformation being further such as to establish a second generally U-shaped projection of the coil in a second viewing aspect which is normal to the coil axis, said viewing aspects being orthogonally related. The depth of the deformation is common to each of the U-shapes and is approximately one fourth of the combined span of the two U-shapes.

8 Claims, 12 Drawing Figures

COIL CONSTRUCTION FOR ELECTROMAGNETIC TREATMENT OF AN AFFLICTED BODY REGION

BACKGROUND OF THE INVENTION

This invention relates to the treatment of living tissues and/or cells by altering their interaction with charged species in their environment. More particularly, the invention relates to an electromagnetic body-treatment device for surgically non-invasive modification of the growth, repair and maintenance behavior of living tissues and cells by a specific and selective change in electrical environment.

Ryaby, et al. U.S. Pat. Nos. 4,105,017, 4,266,532 and 4,266,533 describe means for effecting surgically non-invasive direct inductive coupling to an afflicted body region, whereby one or more electric voltage and concomitant current signals conform to a highly specific pattern and have been found to develop therapeutically beneficial treatment of the afflicted region, as for example in the enhancement of repair of bone fractures, non-unions, and the like. In general, the involved treatment head or heads have involved one or more large coils, which have served well for the treatment of large-member bones, as in leg regions. And various special-purpose coil and head configurations have been disclosed for specific treatments. In general, it may be said that it has been preferred practice to employ a treatment-head configuration in which two like coils are electrically connected in flux-aiding relation and have flexibly articulated connection to enable strapped application on opposite sides of an afflicted limb, and with the coils on a common axis of magnetic-flux development through the afflicted region; in this situation, as in the vast majority of bone-treating uses of such treatment heads, they are removably applied to the outside of a plaster cast or other means of immobilizing the site to be repaired. The coils are therefore bulky and awkward, and they limit freedom of movement while in use.

Pescatore, U.S. Pat. No. 4,501,265, describes a coil configuration wherein bulk is reduced and use is simplified, in that the configuration is unit-handling, does not require strapping, and yet achieves the effect of two spaced coils driven in flux-aiding direction; this effect results from the particular twisting of a single large coil into a figure-8 pattern, to establish two loops which are then folded to establish these loops in spaced parallel relation on a common axis, and the body member to be treated is interposed between the folded loops.

Talish, et al. pending patent application, Ser. No. 473,801 recognizes the desirability of reducing the bulk and awkwardness of conventional coil-head configurations by designing them for castability, i.e., for embedment within an immobilizing cast. But to achieve assurance of adequate in-depth flux development in a given body member, the coils of said application rely upon the recognized effectiveness of two spaced coils, connected in flux-aiding relation.

BRIEF STATEMENT OF THE INVENTION

It is an object of the invention to provide an improved coil configuration for surgically non-invasive magnetic-field treatment of an afflicted body region.

A specific object is to meet the above object with a single-coil configuration, i.e., with a coil which does not require the cooperative concurrent action of another coil in order to establish a substantial in-depth distribution of relatively uniform magnetic flux.

Another specific object is to meet the above objects with a configuration which is castable, i.e., may be embedded or otherwise contained within the cast or other means of immobilizing the body region of treatment.

Still another specific object is to provide a coil configuration which is uniquely applicable to serve the treatment requirements of an optionally selected one of two different body-limb dimensions.

The invention achieves the foregoing objects and provides further features by so permanently deforming an otherwise flat circular multiple-turn coil as to establish a first generally U-shaped projection of the coil in a first viewing aspect which is normal to the coil axis, the deformation being further such as to establish a second generally U-shaped projection of the coil in a second viewing aspect which is normal to the coil axis, said viewing aspects being orthogonally related. The depth of the deformation is common to each of the U-shapes and is approximately one fourth of the combined span of the two U-shapes.

DETAILED DESCRIPTION

The invention will be illustratively described in detail in conjunction with the accompanying drawings, in which.

Figure 1:
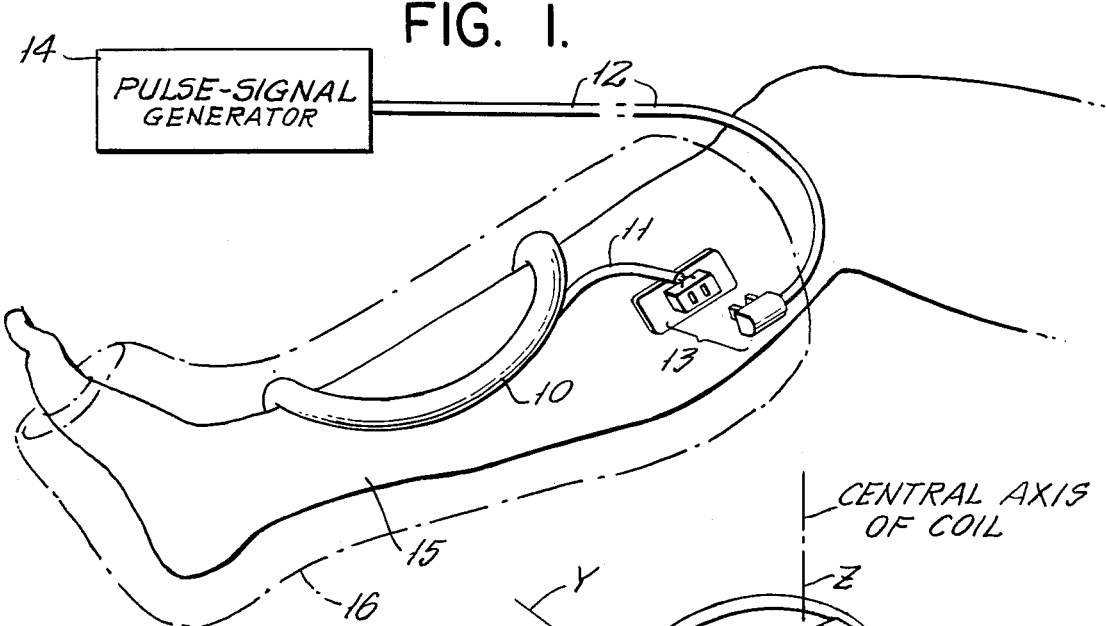
FIG. 1 is a perspective view of a coil configuration of the invention, applied to an afflicted tibia region, with a suggestion of cast immobilization, and connected for electromagnetic treatment of the region.

Referring initially to FIG. 1, the invention is shown in application to a single coil 10 of multiple turns of insulated wire, the ends of the coil having lead connection at 11 to a flexible cable 12 for removable connection via a plug 13, to a pulse-signal generator 14. Such a signal generator and the character of signals produced thereby have been described in said Ryaby, et al. patents, so that further description thereof is not now needed. The coil 10 is shown applied directly to the adjacent contour of a human leg 15, wherein it is assumed for present illustrative purposes that a fracture, which may be a fresh fracture or a non-union, exists in the involved tibia. A phantom outline 16 is suggestive of an orthopedic cast in which coil 10 is embedded or otherwise contained; and the plug means 13 may be of a variety shown in said Talish, et al. application, wherein a plug receptacle is adhesively applied to the skin and becomes a consolidated part of the cast, providing external detachable access to the pulse-signal generator 14.

The general shape of coil 10 may be described by saying that it is deformed from an initially flat circular shape, into an ellipse wherein the major axis is directed along and adjacent the shin of leg 15, and the coil is further deformed so as to generally conform the minor axis of the ellipse to the adjacent sectional contour of leg 15.

Figure 2:
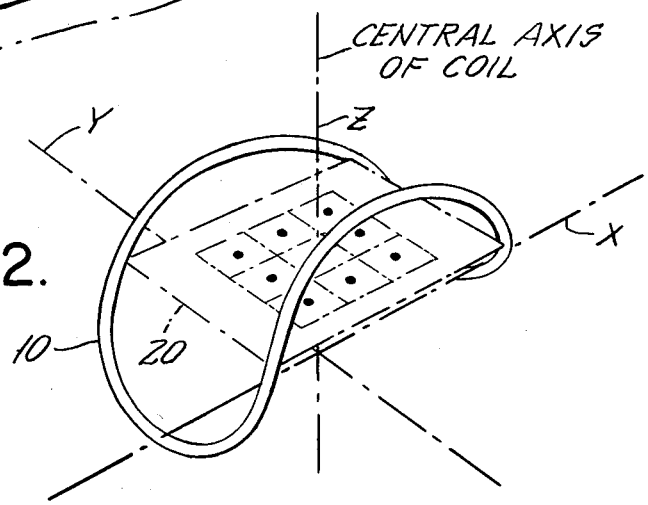
FIG. 2 is a view in similar perspective, with imaginary construction lines to facilitate description.
Figure 3:
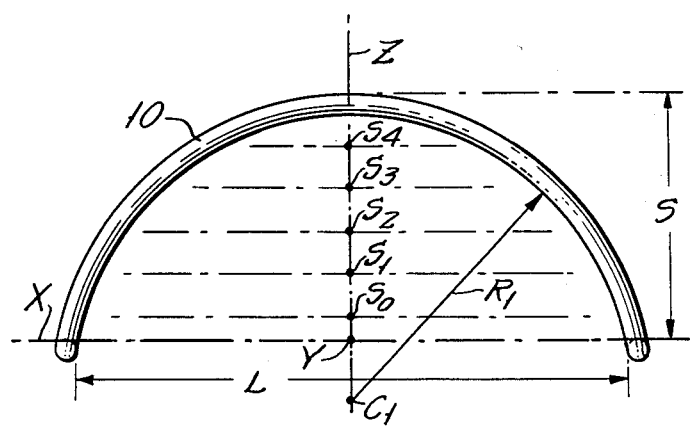
FIGS. 3 and 4 are views of the coil of FIGS. 1 and 2, from orthogonally related viewing aspects which are normal to the central axis of the coil.
Figure 4:
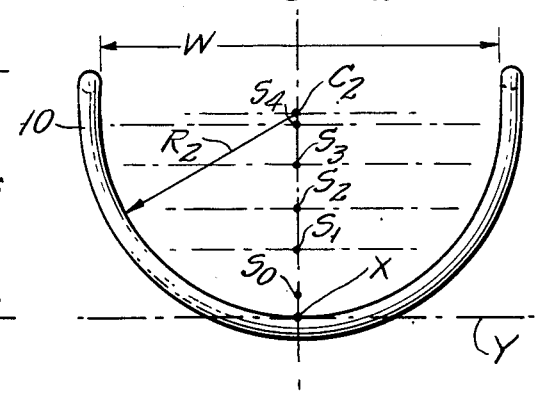

It is more convenient and more accurate to have reference to FIGS. 2, 3 and 4 for a better description of the configuration of coil 10. In FIG. 2, orthogonal axes X-Y define a plane which is normal to the central axis Z of coil 10, the plane X-Y being shown for the condition Z=0, namely, when the X-axis is tangent to the upper surface of coil 10 and is in close parallel adjacency to the major axis of coil 10. The X-Y plane appears as the line X in FIG. 3, with the axis Y a central point thereon; and the X-Y plane appears as the line Y in FIG. 4, with the axis X a central point thereon.

It is important to the invention that application of coil 10 to the body member 15 shall inherently establish a relatively uniform in-depth distribution of magnetic flux within the overall prismatic volume defined by the coil. To this end, a depth dimension S is identified in FIG. 3, the depth S being measured along the central or Z axis, from the zero or reference plane X-Y to the maximum upper extent of the coil. In FIG. 3, a view in the direction along the Y axis shows coil 10 to have its greater span L between ends of a generally U-shape which is arcuate about a first radius $R_1$, wherein the center $C_1$ of the arc is below (i.e., outside of) the overall prismatic volume defined by the coil. And in FIG. 4, a view in the direction along the X axis shows coil 10 to have its lesser span W between ends of another generally U-shape which is arcuate about a second radius $R_2$, wherein the center $C_2$ of this second arc is within the overall prismatic volume defined by the coil. The dimensions of the prismatic volume are thus $S \times L \times W$.

For the illustrated case wherein the arcuate curvature for the respective viewing aspects (FIGS. 3 and 4) for coil 10 are circular arcs, the preferred relation of dimensions is given by the expression:

$$S = k\left(\frac{R_1 + R_2}{2}\right), \quad (1)$$

where the factor k is preferably near unity, and within the range 0.5 to 1.5. Such a range includes the proportions shown for FIGS. 3 and 4; and it will also be understood to include proportions wherein $R_1$ and $R_2$ are equal or nearly equal.

Figure 5:
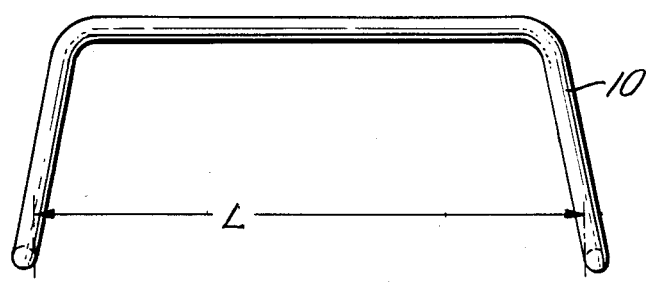
FIGS. 5 and 6 are simplified views corresponding to FIGS. 3 and 4, but for a modification.
Figure 6:
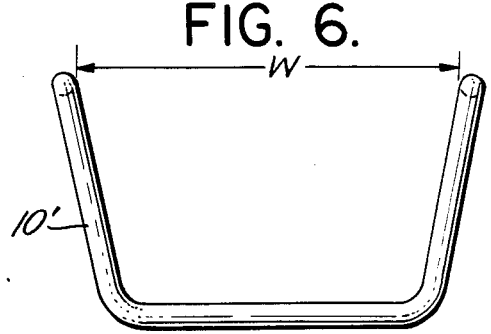
Figure 7A:
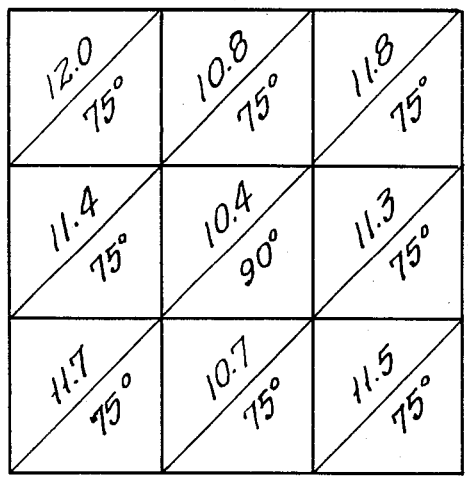
FIGS. 7a to 7f are plots of field measurement of induced-voltage and B-vector direction, for different depths within an included volume of effectiveness of a coil of the invention.
Figure 7B:
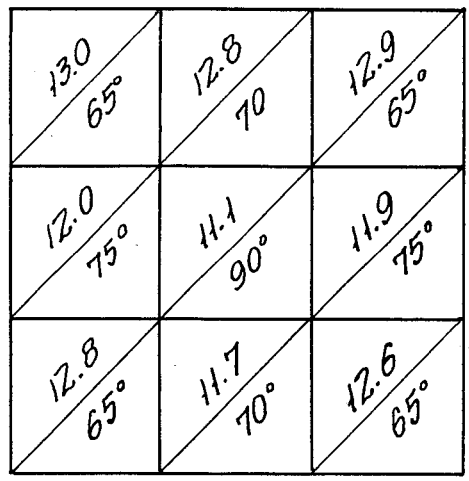
Figure 7C:
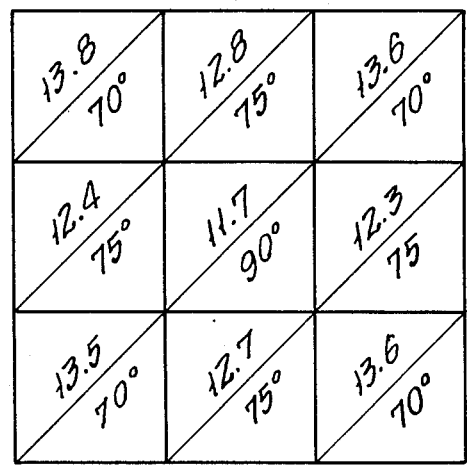
Figure 7D:
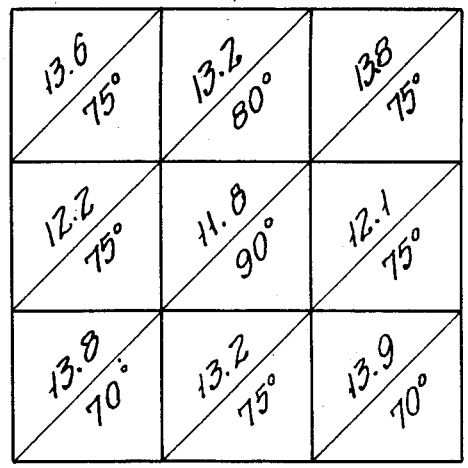
Figure 7E:
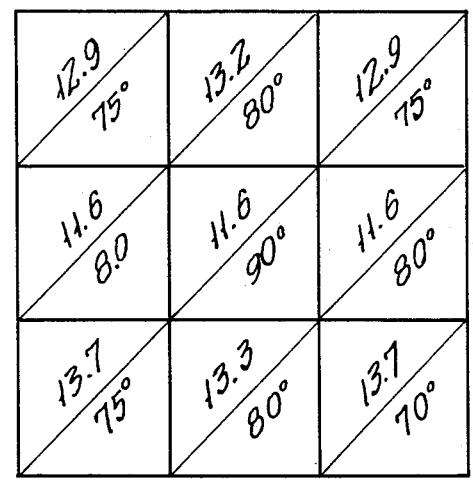
Figure 7F:
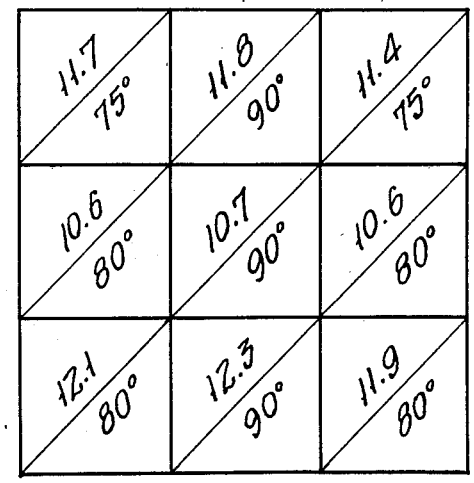

FIGS. 5 and 6 are generally similar to and correspond to FIGS. 3 and 4, except that the U-shapes for the respective orthogonal aspects of view of a coil 10' are more rectangular, with major and minor spans L and W, respectively. For such situations, it is convenient to express the preferred relationship as:

$$S = k\left(\frac{L + W}{4}\right), \quad (2)$$

where k is again in the range 0.5 to 2.0. The fact of the matter is that this relation (2) is a good generic expression for the preferred relationship, whatever the rectilinear or curvilinear nature of all or part of one or both of the U-shapes. For this reason, the span dimensions L and W of FIGS. 3 and 4 may be considered applicable to Equation (2) above.

In FIGS. 3 and 4, graduations $s_0, s_1, s_2, s_3, s_4$, suggestively mark increments of progressive depth into limb 15, it being noted that $s_0$ is at offset from the X-Y plane to allow for the fact that there will always be approximately this much flesh between any bone and any outer contact with adjacent skin. These increments may be illustratively deemed to be at 1-cm. intervals, which therefore comprehend a useful depth of magnetic-field development, fully embracing the depth of the involved tibia and therefore embracing any non-union of such depth extent; illustratively, the depicted coil 10 may have the dimensions S=6.5 cm., L=13.5 cm., and W=10 cm., in which case the factor k is 1.1. For a coil of these proportions, I have made magnetic field-strength measurements in each of the planes that are parallel to the X-Y plane, for the respective depths $s_1 \ldots s_4$, and beyond and have established that along the Z axis, for the span S, and even beyond for two more such increments ($s_5, s_6$, not shown), the field strength remains constant well within ±15%, which is a range that for therapeutic purposes can be taken as substantially constant.

More specifically, for the particular coil configuration described above, these field measurements have been made within lateral limits of offset from the Z axis, for each of the various offset planes, exemplified by the plane 20 shown by phantom outline in FIG. 2, being the plane at the depth location $s_2$ of FIGS. 3 and 4. And FIGS. 7a through 7f separately report the measurements at the respective planes $s_1$ through $s_6$, in each case via a two-dimensional grid in the applicable plane, where elemental areas are 2-cm. squares, with a heavy dot being shown at the center of each square for the illustrated plane 20 in FIG. 2, to mark the location of each measurement.

In the grids of FIGS. 7a through 7f, each elemental square is diagonally divided, to show measured millivolts and the inclination of the B vector to the plane of measurement. For all measurements, the coil was excited by the same Ryaby, et al. pulsed signal, and induced-voltage measurement was made by a small field coil as also described in said Ryaby, et al. patents. For the six depths expressed by these measurements, the probed volume is essentially that of a cube with 6-cm. sides, and all induced voltages are within limits of 10.4 and 13.9 millivolts, which can be seen to be within ±15% of a median induced voltage of 12.15 millivolts. The fact that B-vector direction varies is not deemed significant in view of the fact that each cell is independently affected by magnetic field strength only at its own site, and therefore the field-strength vector direction at any adjacent site is immaterial.

It will be seen that the described coil configuration and criteria meet all stated objects and lend themselves to a variety of dimensional relationships, including those in which the dimensions L and W are equal or substantially equal to each other, as well as those in which the depth span S is equal or substantially equal to one half of each of the dimensions L and W. For the illustrated case of FIGS. 1 to 4, the treated body member happens to be relatively narrow, so that FIG. 4 illustrates the leg-wrapping contour that is involved. However, for a femur non-union or other impairment, the involved thigh is considerably thicker, so that a wrapped application to the body will be about the larger-span curvature, as seen in FIG. 3. Thus, for any one coil meeting the stated criteria of proportional relationships, wherein the span L is different from the span W, the invention provides optional application whereby a selected one of two different body-dimensional situations can be served by a single coil.

While the invention has been shown and described for specific embodiments, it will be understood that modifications may be made without departing from the scope of the invention.

What is claimed is:

1. An electromagnetic body-treatment device for surgically non-invasive modification of the growth, repair and maintenance behavior of living tissues and cells by a specific and selective change in electrical environment, comprising a single multi-turn electrical coil of initially generally circular configuration, wherein a central axis of symmetry extends normal to the plane of said coil, said coil having an external lead-cable connection and said coil being deformed to an extent S out of the plane of said coil into a first body-adapting configuration which is generally U-shaped and generally symmetrically disposed on opposite sides of a first viewing plane defined by said central axis and by a first viewing-aspect axis normal to said central axis, said deformed coil being also in a second body-adapting configuration which is generally U-shaped and symmetrically disposed on opposite sides of a second viewing plane defined by said central axis and by a second viewing-aspect axis normal to said central axis and to said first viewing-aspect axis, the extent S being related to the span L between ends of one of said U-shapes and to the span W between ends of the other of said U-shapes such that $$S = k\left(\frac{L+W}{4}\right),$$

where k is in the range 0.5 to 2.0, and means connected to said cable connection for electrically exciting said single coil with a therapeutically beneficial electrical signal; whereby, upon insertion of an afflicted body region into the U-shaped concavity of one of said configurations, a substantially uniform distribution of magnetic-flux intensity develops in a substantially prismatic volume within the included volume defined by the two U-shaped formations.

2. The body-treatment device of claim 1, wherein the span W is related to the span L in the range 0.5 to 1.0.

3. The body-treatment device of claim 1, wherein the span W and the span L are substantially equal to each other.

4. The body-treatment device of claim 3, wherein the spans W and L are each substantially equal to the extent S.

5. The body-treatment device of claim 1, wherein one of said U-shapes includes a generally circular arc having its center within said included volume and the other of said U-shapes includes a generally circular arc having its center outside said included volume.

6. The body-treatment device of claim 1, wherein one of said U-shapes includes arms having substantially parallel extremities.

7. The body-treatment device of claim 6, wherein the other of said U-shapes includes a substantially straight segment intermediate the arms of said other U-shape.

8. The body-treatment device of claim 1, in which each of said U-shapes includes a generally circular arc.

* * * * *